United States Patent
Schuerch

(10) Patent No.: US 6,704,959 B2
(45) Date of Patent: Mar. 16, 2004

(54) ADJUSTABLE POSITION LIMB SUPPORT FOR SURGICAL TABLES

(76) Inventor: Peter Schuerch, 42 Bayview Ave., Quincy, MA (US) 02169

( * ) Notice: Subject to any disclaimer, the term of this patent is extended or adjusted under 35 U.S.C. 154(b) by 0 days.

(21) Appl. No.: 09/928,002

(22) Filed: Aug. 13, 2001

(65) Prior Publication Data

US 2003/0028967 A1 Feb. 13, 2003

(51) Int. Cl.$^7$ ................................................. A61G 7/075
(52) U.S. Cl. ..................... 5/648; 5/646; 5/649; 5/651; 5/623; 5/624
(58) Field of Search ............................. 5/648, 624, 623, 5/621, 620, 612, 649, 656, 651; 248/229.1, 229.14, 229.15, 229.22

(56) References Cited

U.S. PATENT DOCUMENTS

| | | | | | |
|---|---|---|---|---|---|
| 2,642,250 A | * | 6/1953 | Kasnowich | ............... | 248/229.1 |
| 3,046,072 A | * | 7/1962 | Douglass, Jr. et al. | .......... | 5/646 |
| 5,281,001 A | * | 1/1994 | Bergsten et al. | ............... | 35/646 |
| 5,369,827 A | * | 12/1994 | Parke et al. | .................... | 5/649 |
| 5,560,577 A | * | 10/1996 | Keselman | ....................... | 5/624 |
| 5,582,379 A | * | 12/1996 | Keselman et al. | ............. | 5/624 |
| 5,802,641 A | * | 9/1998 | Van Steenburg | ............... | 5/648 |
| 5,918,330 A | * | 7/1999 | Navarro et al. | ................. | 5/624 |
| 6,058,534 A | * | 5/2000 | Navarro et al. | ................. | 5/648 |
| 6,263,531 B1 | * | 7/2001 | Navarro et al. | ................. | 5/648 |
| 6,276,651 B1 | * | 8/2001 | Dolan | ................... | 248/229.22 |

* cited by examiner

Primary Examiner—Frederick Lyndon Lagman
(74) Attorney, Agent, or Firm—John M. Brandt

(57) ABSTRACT

An adjustable position limb support for surgical tables consisting of a support arm pivotally mounted at one end to a base which is attachable to the table and an externally powered position actuator pivotally mounted to the support arm and the base at positions spaced apart from the support arm pivot. The actuator is extendable and retractable and may be powered either electrically, hydraulically, or by compressed air. The actuator is controlled by a suitable device within the actuator or remote from it and an appropriate appliance for holding the limb is provided on the support arm.

5 Claims, 3 Drawing Sheets

ADJUSTABLE POSITION LIMB SUPPORT FOR SURGICAL TABLES

BACKGROUND OF THE INVENTION

1. Field of the Invention

The invention resides in the field of limb supports for surgical procedures and more particularly relates to supports adjustable over a selected range of positions.

2. Description of the Prior Art

Adjustable supports for immobilizing limbs during surgical procedures, whether the surgery is performed on the limb or another part of the body near the limb, are known in the prior art. In particular there are positioning devices incorporating ratchet mechanisms which lock into place at preselected positions. Further U.S. Pat. No. 6,058,534, Navarro et al., discloses a support infinitely adjustable over a selected range using a compressed gas locking cylinder which may be secured or locked in a desired position and then unlocked to reposition the support.

While the locking cylinder provides a level of assistance, the support must none the less be manually lifted or lowered by the surgeon or an assistant to reposition the limb during surgery.

In contrast, the present invention eliminates the need for such manual manipulation by providing an externally powered limb support actuator which may be controlled by the surgeon or an assistant without interruption of the surgical procedure to make any required adjustments.

SUMMARY OF THE INVENTION

The invention may be summarized as a limb, i.e., arm or leg support, arranged to hold and immobilize the limb in a variable selected position during a surgical procedure. The device consists of a base attachable to a surgical table, a post attachable by a clamp for example; a support arm pivotally attached to the base; and an extendable and retractable externally powered position actuator pivotally mounted to both the support arm and the base. The actuator may comprise an electrically powered linear actuator having a motor and screw assembly to provide displacement or a compressed air or hydraulic actuator. A control system is provided to extend or retract the integral operating arm which is driven by one of the above named power sources and may be in the form of push buttons mounted on the actuator or hand held and remotely connected by wire or a foot switch or the like. An appropriate limb holding device attached to the support rod, a surgical boot for example, completes the invention.

As the device is powered by an external source, repositioning the limb is independent of gravity and the lifting force, which must be supplied by the operator in prior art devices. Further, minute changes of position may be accomplished without the surgeon discontinuing the operating procedure, and without any likelihood of mispositioning by an assistant or the surgeon themselves as might happen if they are required to leave the operating site to perform an adjustment. Additionally, the danger of slippage resulting in potential injury to a patient is eliminated since a positive control act must be performed to reposition the support arm. This can only take place at the operating speed of the actuator.

These and other features and advantages of the invention will become more clear from the description of the preferred embodiment and drawings which follows.

DESCRIPTION OF THE PREFERRED EMBODIMENT

Figure 1:
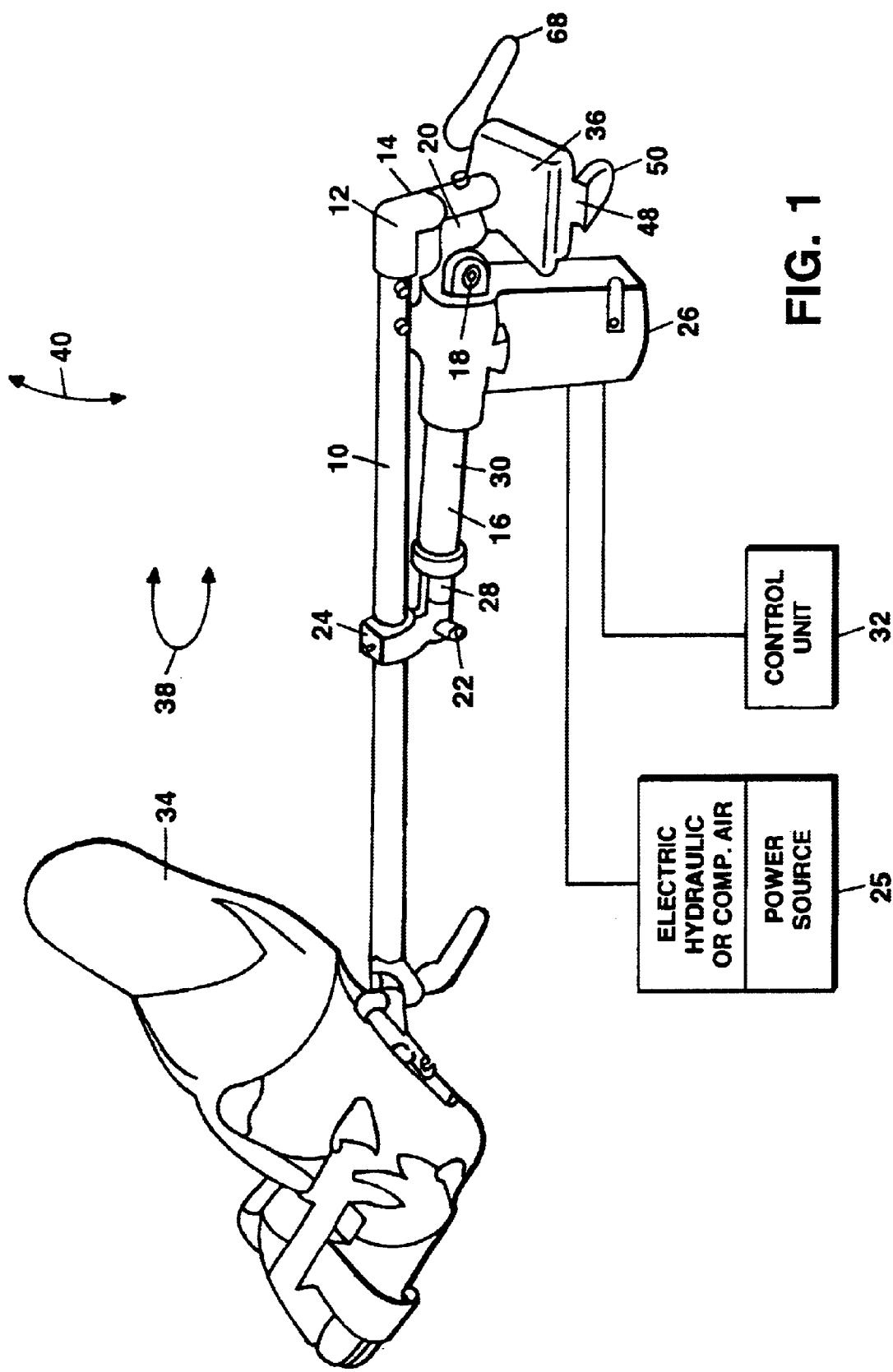
FIG. 1 is a perspective view of the preferred embodiment of the invention.

Referring first to FIG. 1, there is shown the preferred embodiment of the invention in which limb support arm 10 is pivotally attached at 12 to a base member comprising, for example, a post 14. An actuator 16 has one end pivotally attached at 18 to an extension 20 of post 14 forming an additional portion of the base member.

The opposite end of actuator 16 is pivotally attached at 22 to support arm collar 24 which forms an extension of support arm 10. Actuator 16 comprises, for example, an electrically powered linear actuator having a worm gear motor disposed in casing 26 powered by a source shown schematically at 25, and a threaded spindle 28 disposed in casing extension 30. The power source and associated motor are preferably electrical but hydraulic or compressed air devices may also be used. A control unit shown schematically at 32 operates the motor. The unit may comprise either a hand held or foot operated mechanism. A limb support device, a surgical boot 34 for example, completes the device.

Post 14 may be attached to a surgical table by a variety of means, and, as shown by mounting clamp 36, the details of which will be described in more detail below, Post 14 rotates in clamp 36 to provide position adjustment in the relatively horizontal plane (the axis) 38, while operation of the actuator by extension or retraction provides position adjustment in the relatively vertical plane (the axis) 40. As will be seen, extension of spindle 28 will cause support arm 10 to rotate upwards about pivot 12 and retraction of the spindle to rotate downwards.

Figure 2:
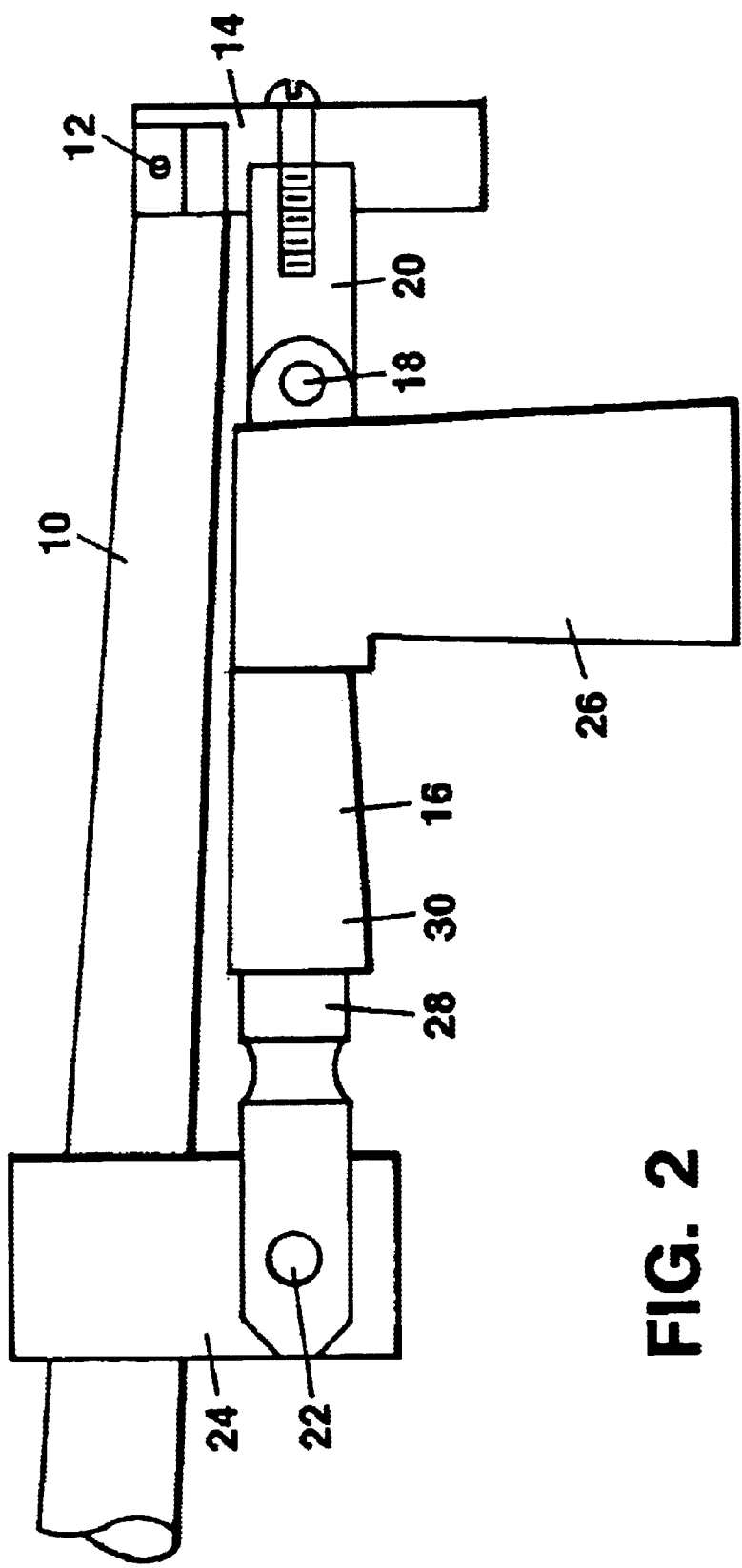
FIG. 2 is a partial cross-sectional view of the embodiment of FIG. 1.

Referring next to FIG. 2, a partial cross-sectional view of the preferred embodiment of FIG. 1 is shown to further clarify the mechanical construction of the invention. Like numbers refer to like components.

A suitable electrically operated actuator comprising the components shown as 16, 26, 28, and 30 and appropriate control devices are available as a product termed the ECO-MAG from Magnetic AG, Liestal, Switzerland.

Figure 3:
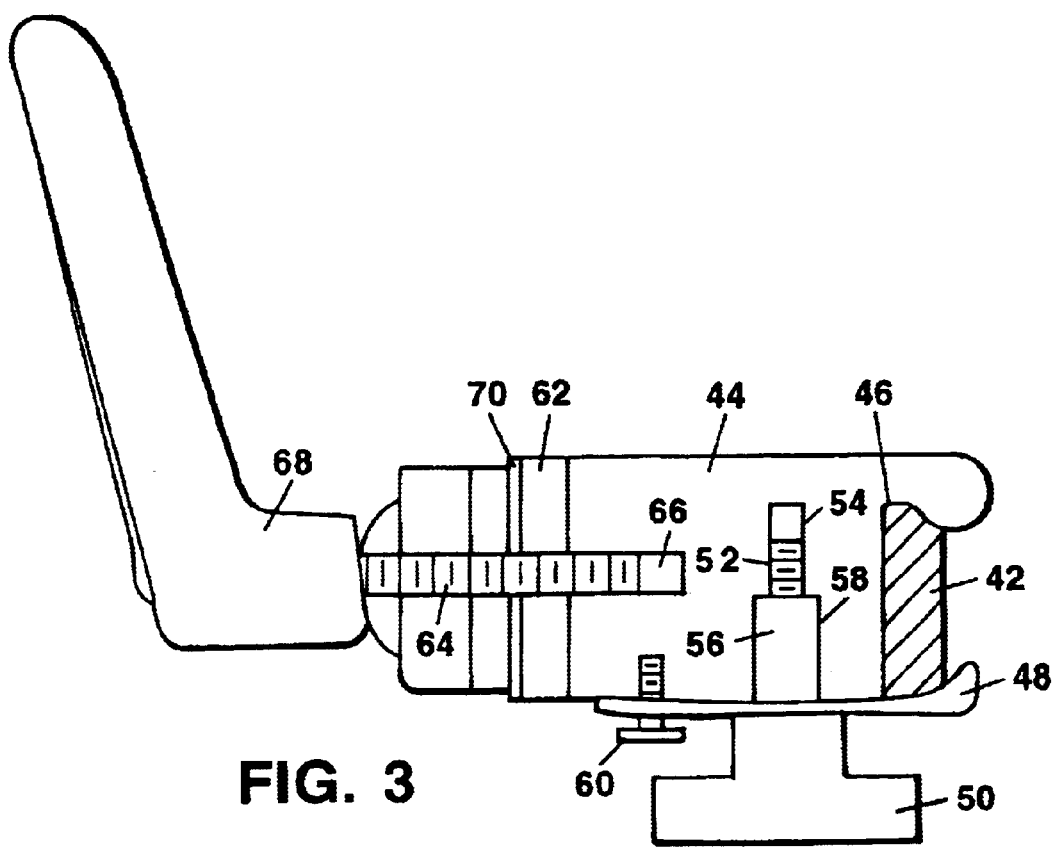
FIG. 3 is a partial cross-sectional side view of an additional component of FIG. 1.

FIG. 3 illustrates the construction of mounting clamp 36 in a partial cross-sectional view. The clamp is attachable to a surgical operating table rail 42 by clamping pressure exerted between the clamp body 44 having rail receiving recess 46 and plate 48 which is biased upward by handle 50 having bolt 52 cooperatively engaged with threaded chamber 54. Spring 56 disposed in chamber 58 over bolt 52 biases plate 48 and handle 50 outward while turnscrew 60 prevents the plate from rotating out of position prior to attachment.

Figure 4:
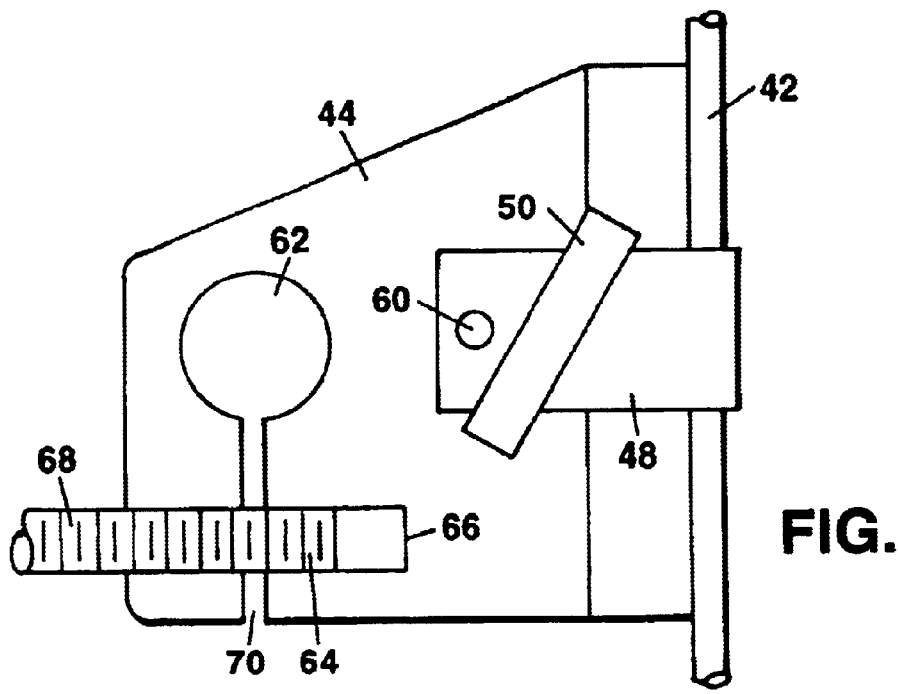
FIG. 4 is bottom view of the component of FIG. 3.

Port 62 is arranged to receive post 14 which may be clamped in place by bolt 64 cooperatively engaged with threaded chamber 66 and attached to handle 68. Upon rotating handle 68 and tightening bolt 64, the portion of body 44 adjacent port 62 is squeezed as allowed by slot 70, more clearly illustrated in FIG. 4 wherein like numbers refer to like components. The port is thus contracted sufficiently to secure the post and support arm in a desired rotational position. This position may then be shifted by loosening the bolt, rotating the post and arm and then retightening.

As variations in the above described preferred embodiment will now become obvious to those skilled in the art, the invention is accordingly defined by the following claims.

What is claimed is:

1. An adjustable position limb support for surgical tables comprising in combination:
   a. a base member attachable to a surgical table;
   b. a limb support arm having a limb support arm pivot pivotally attached at one end to said base member;
   c. an extendable and retractable electrically powered position actuator having a first actuator pivot pivotally attached at one end to said base member at a position spaced apart from said limb support arm pivot and having a second actuator pivot pivotally attached to said support arm at a position spaced apart from said limb support arm pivot;
   d. limb means attached to said support arm for securing said limb to said support arm; and
   e. control means for extending and retracting said actuator whereby, upon operation of said control means, the position of said support arm and said limb will be adjusted in relation to said table.

2. The apparatus of claim 1 wherein said base member comprises a post.

3. The apparatus of claim 2 wherein said base member further includes a clamp attachable to a surgical table and wherein said clamp has a port for rotationally receiving said post.

4. An adjustable position limb support for surgical tables comprising in combination:
   a. a base member attachable to a surgical table, said base member comprising a post and a clamp for attaching said post to a rail of a surgical operating table, said clamp comprising in combination:
      i. a clamp body for engaging one edge of said rail, said body having a lip to fit over said edge;
      ii. a plate for engaging the opposite edge of said rail, said plate having a lip to fit over said opposite edge;
      iii. first bolt means disposed in said clamp body engaging said plate for biasing said plate against said opposite edge;
      iv. a port for receiving said post;
      v. a slot having two opposing edges traversing said body and communicating with said port; and
      vi. second bolt means disposed in said clamp body traversing said slot for biasing one edge of said slot towards the other whereby upon rotating said second bolt means, said post will be held or released from said port;
   b. a limb support arm having a limb support arm pivot pivotally attached at one end to said base member;
   c. an extendable and retractable electrically powered position actuator
      having a first actuator pivot pivotally attached at one end to said base member at a position spaced apart from said limb support arm pivot and having a second actuator pivot pivotally attached to said support arm at a position spaced apart from said limb support arm pivot;
   d. limb holding means attached to said support arm for securing said limb to said support arm; and
   e. control means for extending and retracting said actuator whereby, upon operation of said control means, the position of said support arm and said limb will be adjusted in relation to said table.

5. The apparatus of claim 4, wherein said clamp further comprises a handle attached to each of said bolts.

* * * * *